US012558358B2

(12) United States Patent
Voller et al.

(10) Patent No.: US 12,558,358 B2
(45) Date of Patent: Feb. 24, 2026

(54) N-(FURAN-2-YLMETHYL)-7H-PURIN-6-AMINE FOR TREATMENT OF CIRCADIAN RHYTHM DISEASES, DISORDERS AND DYSFUNCTIONS

(71) Applicants:UNIVERZITA PALACKEHO V OLOMOUCI, Olomouc (CZ); FYZIOLOGICKY USTAV AV CR, V. V. I., Prague (CZ)

(72) Inventors: Jiri Voller, Brno (CZ); Martin Sladek, Prague (CZ); Marian Hajduch, Norbercany (CZ); Alena Sumova, Prague (CZ); Miroslav Strnad, Olomouc (CZ)

(73) Assignees: UNIVERZITA PALACKEHO V OLOMOUCI, Olomouc (CZ); FYZIOLOGICKY USTAV AV CR, V. V. I., Prague (CZ)

( * ) Notice: Subject to any disclaimer, the term of this patent is extended or adjusted under 35 U.S.C. 154(b) by 770 days.

(21) Appl. No.: 17/781,629

(22) PCT Filed: Dec. 8, 2020

(86) PCT No.: PCT/CZ2020/050094
§ 371 (c)(1),
(2) Date: Jun. 1, 2022

(87) PCT Pub. No.: WO2021/115502
PCT Pub. Date: Jun. 17, 2021

(65) Prior Publication Data
US 2023/0039704 A1 Feb. 9, 2023

(30) Foreign Application Priority Data
Dec. 9, 2019 (CZ) ................................ CZ2019-757

(51) Int. Cl.
| | |
|---|---|
| A61K 31/52 | (2006.01) |
| A61K 31/05 | (2006.01) |
| A61K 31/10 | (2006.01) |
| A61K 31/136 | (2006.01) |
| A61K 31/165 | (2006.01) |
| A61K 31/175 | (2006.01) |
| A61K 31/198 | (2006.01) |
| A61K 31/282 | (2006.01) |
| A61K 31/343 | (2006.01) |
| A61K 31/4045 | (2006.01) |
| A61K 31/4184 | (2006.01) |
| A61K 31/475 | (2006.01) |
| A61K 31/655 | (2006.01) |
| A61K 31/675 | (2006.01) |
| A61K 33/243 | (2019.01) |
| A61P 25/20 | (2006.01) |
| A61P 35/00 | (2006.01) |

(52) U.S. Cl.
CPC .............. *A61K 31/52* (2013.01); *A61K 31/05* (2013.01); *A61K 31/10* (2013.01); *A61K 31/136* (2013.01); *A61K 31/165* (2013.01); *A61K 31/175* (2013.01); *A61K 31/198* (2013.01); *A61K 31/282* (2013.01); *A61K 31/343* (2013.01); *A61K 31/4045* (2013.01); *A61K 31/4184* (2013.01); *A61K 31/475* (2013.01); *A61K 31/655* (2013.01); *A61K 31/675* (2013.01); *A61K 33/243* (2019.01); *A61P 25/20* (2018.01); *A61P 35/00* (2018.01)

(58) Field of Classification Search
CPC ...... A61K 31/52; A61K 33/243; A61K 31/05; A61K 31/10; A61K 31/136; A61K 31/165; A61K 31/175; A61K 31/198; A61K 31/282; A61K 31/343; A61K 31/4045; A61K 31/4184; A61K 31/475; A61K 31/655; A61K 31/675; A61P 25/20; A61P 35/00
See application file for complete search history.

(56) References Cited

FOREIGN PATENT DOCUMENTS

| | | | |
|---|---|---|---|
| CN | 101797280 B | 11/2011 | |
| CN | 109833338 A | 6/2019 | |
| IE | 20150193 A1 * | 1/2017 | ............. A61K 31/00 |
| TW | 201109318 A | 3/2011 | |
| WO | 03051356 A1 | 6/2003 | |
| WO | 2015123365 A1 | 8/2015 | |

OTHER PUBLICATIONS

Honig, International Journal of Molecular Sciences, Dec. 14, 2018; 19(12):4045 (Year: 2018).*
Pandi-Perumal, Ageing Research Reviews, vol. 1, Issue 3, Jun. 2002, pp. 559-604) (Year: 2002).*
Shen, Acta Biochim Biophys Sin, 2019, 51 (8), 834-844, Published: Jul. 17, 2019 (Year: 2019).*
The Cleveland Clinic, Jet-Lag, https://web.archive.org/web/20250726165922/https://my.clevelandclinic.org/health/diseases/12781-jet-lag (Year: 2025).*
D'Ettorre, Safety and Health at Work, 11, 2020, 244-247 (Year: 2020).*
Roenneberg, Biology (Basel), Jul. 12, 2019; 8(3) (Year: 2019).*
CN 109833338 English Translation (Year: 2019).*
Kadlecova Alena et al: "The plant hormone kinetin in disease therapy and healthy aging", Ageing Research Reviews, Elsevier, Amsterdam, NL, vol. 55, Aug. 31, 2019 (Aug. 31, 2019), XP085850413, ISSN: 1568-1637, DOI: 10.1016/J.ARR.2019.100958, http://dx.doi.org/10.1016/j.arr.2019.100958, retrieved Jun. 1, 2022.
(Continued)

*Primary Examiner* — Andrew D Kosar
*Assistant Examiner* — Phillip Matthew Rzeczycki
(74) *Attorney, Agent, or Firm* — Notaro, Michalos & Zaccaria P.C.

(57) ABSTRACT
N-(furan-2-ylmethyl)-7H-purin-6-amine, or a pharmaceutically acceptable salt or solvate thereof, for prevention and/or treatment of circadian rhythm disorders, circadian rhythm diseases and/or circadian rhythm dysfunctions is disclosed. The disorders, diseases and dysfunctions include, inter alia, jet-lag, social jet-lag, shift-work disorder, and circadian rhythm disturbance induced by neurodegeneration is also disclosed.

4 Claims, 7 Drawing Sheets

(56)                      References Cited

OTHER PUBLICATIONS

Levi Francis et al: "Circadian Timing in Cancer Treatments",
Annual Review of Pharmacology and Toxicology., vol. 50, No. 1,
Feb. 1, 2010 (Feb. 1, 2010), pp. 377-421, XP05577 4660, us ISSN:
0362-1642, DOI: 10.1146/annurev.pharmtox.48.113006.094626
Retrieved from the Internet: URL:https://www.annualreviews.org/
doi/pdf/10.1146/annurev.pharmtox, retrieved Jun. 1, 2022.
International Search Report and Written Opinion for corresponding
PCT application No. PCT /CZ2020/050094, mailed Feb. 22, 2021.

* cited by examiner

N-(FURAN-2-YLMETHYL)-7H-PURIN-6-AMINE FOR TREATMENT OF CIRCADIAN RHYTHM DISEASES, DISORDERS AND DYSFUNCTIONS

FIELD OF ART

The invention relates to the use of N-(furan-2-ylmethyl)-7H-purin-6-amine (kinetin, N6-furfuryladenine, 6-furfurylaminopurine) for modulating circadian rhythms of mammals, including humans, and their cells, tissues and organs. Such modulation is useful for the treatment of both acute and chronic circadian rhythm dysfunctions and circadian rhythm diseases and disorders due to genetic or socio-environmental factors.

BACKGROUND ART

The circadian clock (circadian rhythm) has evolved as an adaptation to a 24-hour solar day, and although its mechanism varies from organism to organism, it is one of the universal characteristics of life. Clock makes it possible to anticipate and prepare for regularly changing external conditions. However, it can also function in aperiodic conditions with its own genetically determined circadian period. Clock is entrainable (i.e. has ability to be synchronized) by the external cues (e.g. light, temperature, social interaction) and controls metabolic, physiological and behavioral rhythms. In mammals, circadian rhythms are controlled by a central pacemaker located in the suprachiasmatic nucleus of the hypothalamus (SCN), which is directly synchronized by light and regulates the local clock in other brain and peripheral tissues such as in the cerebral cortex, hippocampus, retina, liver, kidney, intestine, or pancreas. The main oscillator in the SCN, as well as the peripheral oscillators, are composed of interconnected transcriptional and (post) translational feedback loops (TTFLs) formed by families of clock genes such as Per, Bmal, Clock, Rev-Erb, Ror and Cry. Clock genes then rhythmically regulate a large group of predominantly tissue-specific clock-controlled genes with various functions, including regulation of metabolism, behavior, or cell division.

Interestingly, clock genes play a role in a number of other processes. For example, human ARNTL/BMAL1 upregulates myogenesis and downregulates adipogenesis through transcriptional control of Wnt signaling pathway genes. It also contributes to the normal function of pancreatic beta cells and regulates glucose-stimulated insulin secretion. It further regulates the mTORC1 signaling pathway by regulating MTOR and DEPTOR expression. Chemokine expression in Ly6C monocytes is also regulated by ARNTL/BMAL1. It further regulates the expression of genes involved in hair growth. It also plays an important role in adult hippocampal neurogenesis by timing the entry of neuronal stem cells into the cell cycle. Human PER2 plays a role in lipid metabolism (by suppressing the proadipogenic activity of PPARG) and in glucose metabolism (regulation of circulating insulin levels). PER2 contributes to the maintenance of cardiovascular function by regulating the production of NO and vasodilating prostaglandins in the aorta. It also regulates the absorption of glutamate in synaptic vesicles, the absorption of fatty acids in the liver and is involved in the regulation of inflammatory processes. Clock-controlled genes and proteins can make up more than 20% of the total transcriptome and proteome, depending on the tissue. Many of these genes are associated with serious human diseases, including cancer (WEE1, p21, Ballesta et al. 2017 [doi: 10.1124/pr.116.013441]), myocardial infarction (PA1-1, SCA1, Crnko et al. 2019 [doi: 10.1038/s41569-019-0167-4], Sheer and Shea, 2014 [doi: 10.1182/blood-2013-07-517060]), sleep disorders (CK1d, PER2, CLOCK, PER3, Jones et al. 2013 [doi: 10.1016/j.expneurol.2012.07.012]) or depressive disorder (NFSC, SLC25A17, MEIS1, Ferguson et al. 2018 [https://doi.org/10.1016/j.ebiom.2018.08.004]). Their rhythmic regulation allows cells, tissues and organs to perform physiological processes in a coordinated way, to anticipate and prepare for changes in the environment. Synchronization of individual oscillators in peripheral tissues by the SCN via hormonal and neuronal signals allows precise coordination and integration of various physiological functions.

Dysfunctions of the circadian rhythm in terms of changes in period, phase or amplitude at the level of cells, tissues, organs or the whole body as well as phase mismatch between oscillators in individual tissues/organs or between biological and external time lead to disruption of homeostasis, resulting in various pathologies. Examples of conditions associated with circadian rhythm dysfunction or impairment are: depressive disorder, unipolar depression, bipolar disorder, seasonal affective disorder, dysthymia, anxiety disorder, schizophrenia, Alzheimer's disease, REM sleep disorders, FASPS, ASPD, delayed sleep syndrome phases and free-running sleep phases, hypersomnia, parasomnia, narcolepsy, nocturnal enuresis, metabolic syndrome and obesity, hyperinsulinemia, type 2 diabetes and restless legs syndrome (Jones et al. 2013 [doi: 10.1016/j.expneurol.2012.07.012); Marcheva et al., 2010 [doi: 10.1038/nature09253]; Kalsbeek, 2013 [doi: 10.2337/db12-0507]; Suli et al., 2019 [10.1016/j.trecan.2019.07.002]). Growing evidence also points to an association of circadian rhythm disorders and cancer (Ballesta et al. 2017 [doi: 10.1124/pr.116.013441]; Panda 2019 [doi: 10.1038/s41574-018-0142-x]).

Circadian rhythm disorders may be a result of mutations or epimutations in the molecular components of cellular circadian oscillators, but may also be the result of disease-induced impairment of homeostasis. Abnormal sleep patterns are typical, for example, of a variety of neurological disorders, such as Alzheimer's disease (Weiss et al. 2016 [doi: 10.1371/journal.pone.0146200]), Huntington's disease, Parkinson's disease (Videnovic et al., 2017 [doi: 10.1016/j.nbscr.2016.11.001]) Smith-Magenis syndrome (Nováková et al. 2012 [doi: 10.1210/jc.2011-2750]), bipolar disorder (Nováková et al. 2014 [10.1111/bdi.12270]) or ADHD (Nováková et al. 2011 [doi: 10.3109/07420528.2011.596983]). Impaired rhythms are often also one of the first signs of emerging neurological disorders. For example, one of the consequences of Alzheimer's disease is that long before patients develop symptoms of dementia, circadian rhythms in release of pineal hormone melatonin are disrupted and vasopressin levels in the SCN are reduced. Aging also increases the prevalence of abnormal sleep patterns—for example, elderly patients often experience advanced sleep phase syndrome (ASPD) (Terman et al. 2011 [doi: 10.1177/074873049501000207]) which shortens the circadian period, advances the phase, reduces the amplitude and desynchronizes peripheral rhythms. Interestingly, as of yet unidentified, thermolabile substance present in the serum of the elderly is probably responsible for shortening the period and advancing the phase (Pagani et al., 2011 [doi: 10.1073/pnas. 1008882108]), as application of this serum shortens the period and phase shifts rhythms in human cells in vitro.

Circadian rhythm disturbance or mismatch can also be a side effect of pharmacotherapy. For example, some fixed chemotherapy protocols may alter a patient's circadian rhythm and worsen their own treatment outcome (Ortiz-Tudela, 2014 [doi: 10.1007/978-3-642-25950-0_11]). Thus, it is highly desirable to use personalized procedures in chemotherapy (Dakup et al. 2018 [doi: 10.18632/oncotarget.24539]).

In the absence of external stimuli (for example in constant darkness), the endogenous period of circadian rhythm in humans is on average slightly longer than 24 hours. In completely blind subjects unable to synchronize with light, such a period often persists chronically. As a result, their sleep-wake cycle is free-running with respect to external time, which is often associated with negative metabolic, cognitive and emotional consequences.

The discrepancy of the circadian clock with the external time is also a typical feature of modern life. Air travel allows fast movement across time zones, which results in jet lag. Artificial light allows activity independent of natural light, which effectively synchronizes the central oscillator in the SCN. Personal preference for a specific sleep phase (chronotype) and social factors influence the timing of the individual activity and these factors are often in conflict, resulting in a so-called social jet lag (i.e. a chronic difference between the sleep phase on free days and on working days), which has a negative effect on health (Roenneberg and Merrow, 2008 [doi: 0.1016/j.smrv.2007.07.005]). A particularly important factor causing circadian desynchronization is shift work due to its prevalence (more than 17% of the EU workforce is night workers). The result is frequent sleep problems, fatigue and reduced manual and mental performance. Jet lag, social jet lag and shift work significantly affect physiological functions and increase the incidence of lifestyle diseases (Roennberg 2012 [doi: 10.1016/j.cub.2012.03.038]; Roenneberg and Merrow 2016 [doi: 10.1016/j.cub.2016.04.011]). Frequent shift workers also have an increased risk of depression, metabolic syndrome (Costa et al. 2016 [doi: 10.1080/07420520802114193]), breast, prostate and rectal cancer (Sulli et al. 2019 [doi:/ 10.1016/j.trecan.2019.07.002]). For this reason, in 2007 the WHO International Agency for Research on Cancer (IARC) included circadian disruption among probable human carcinogens (Group 2A).

Correction of disturbed circadian rhythms or correction of their mismatch with external time could be used to treat or alleviate symptoms in a number of dysfunctions and diseases. These include those in whom circadian clock dysfunction or mismatch is the primary cause (hereditary advanced sleep syndrome FASPS, ASPD, delayed sleep phase syndrome DSPD, irregular sleep phase and free-running sleep syndrome, and other circadian rhythm sleep disorders), or one of the possible causes of the disease (depressive disorder, unipolar depression, bipolar disorder, seasonal affective disorder, dysthymia, anxiety disorder, schizophrenia, Alzheimer's disease, REM sleep disorders, metabolic syndrome and obesity, hyperinsulinemia, diabetes T2, non-alcoholic steatohepathy, myocardial infarction, breast cancer, prostate cancer, rectal cancer, delirium), as well as those in whom the circadian rhythm disorder is caused by the disease and may contribute to the pathophysiology of the disease (hypersomnia, parasomnia, insomnia, narcolepsy, nocturnal enuresis, restless legs syndrome, sleep apnea, Smith-Magenis syndrome). Improving sleep could be an important consequence of such therapy, as the length of sleep and its quality affect the incidence of metabolic diseases. Adjusting the shortened period and the advanced phase of rhythms caused by the physiological aging process itself could be a very effective way of treating and preventing the sleep problems associated with old age. These problems are so common that one in five seniors takes sleeping pills. Such therapy could also help with subclinical but subjectively poorly tolerated jet lag problems, such as lack of sleep, fatigue, and loss of concentration and performance. This circadian therapy may even be beneficial in asymptomatic patients in whom peripheral rhythms are impaired, for example due to irregular diet.

Circadian dysfunction can be assessed by measuring physiological (such as body temperature, heart activity, actigraphy) or biochemical parameters (melatonin, metabolites, clock gene RNA and protein levels in body fluids). In the case of an inherited disease, it can be diagnosed using DNA diagnostics based on PCR or sequencing.

Circadian rhythm modulators can also be used prophylactically to accelerate the proper resetting of the circadian system after traveling through time zones or during a planned change of activity (e.g., in preparation for shift work or other social activities).

Current approaches to the treatment of circadian rhythm disorders are dominated by various variants of bright light therapy and the use of melatonin or synthetic melatonin receptor agonists. However, these methods also have significant disadvantages. Bright light therapy is considered very inconvenient for many users because it requires exposure to very high levels of light in precise time windows every day (Zee et al., 2013 [doi: 10.1212/01.CON.0000427209.21177.aa.]). It cannot be used in blind patients. Melatonin is only effective in subset of patients with sleep disorders. It is unlikely to have a significant effect, for example, on patients suffering from FASPS, ASPD or jet lag after traveling westwards. It may cause unwanted drowsiness. In addition, there is great individual variability in response to melatonin. Another disadvantage of light or melatonin is that their effect on the rhythm phase is directly dependent on the instantaneous phase of the central clock in the SCN. For example, light applied during a subjective day has no effect on the SCN phase, as it is in that moment in non-responsive zone of the phase-response curve, so it is necessary to time the therapy to the early morning or late evening hours. Therefore, a direct effect on the molecular circadian mechanism could be a new effective way to adjust circadian rhythms. For example, the CK1δ inhibitor (PF670462, Pfizer) is very effective in prolonging the in vitro and in vivo period in mice. Its uses include arrhythmias caused by phase shift (jet lag, neurodegenerative diseases, disorders associated with aging or shift work) and/or shortening of the period (FASPS, ASPD). An important finding is that PF670462 can also be used to restore physiological rhythms fundamentally disrupted due to genetic disruption of VIP receptors in the SCN (which shortens the period and causes rhythm loss similar to some neurodegenerative diseases) or due to constant light (which also first affects the period and then causes a decrease in amplitude leading to complete loss of rhythms) in mice (Meng et al., 2010 [doi:/10.1073/pnas.1005101107]). Another example of a compound that acts directly on the molecular mechanism is nobiletine (He, Nohara et al. 2016 [doi: 10.1016/j.cmet.2016.03.007]), which increases the amplitude of rhythms at the molecular level by acting on nuclear ROR receptors and has recently been used to prevent metabolic syndrome in a diabetic mouse model and restore physiological rhythms in the liver of mice fed a high-fat diet (He, Nohara et al. 2016 [doi: 10.1016/j.cmet.2016.03.007]), or to reduce cognitive defects caused by constant light and midazolam in a mouse model of delirium (Gile, Scott et al. 2018 [doi: 10.1097/20 CCM.0000000000003077]). Similar therapy targeting the molecular mechanism directly will be beneficial in a number of disorders associated with various types of circadian dysfunctions requiring proper synchronization, period length adjustment, a single new phase adjustment, or increased overall rhythm integrity (see above). In addition, unlike light or melatonin therapies, therapy using agents that directly target the molecular mechanism does not require SCN, is equally effective day and night, and its timing in general is unlikely to significantly affect its effect, which can be easily modulated by dose adjustment.

It is known that various physiological processes influenced by pharmacological substances show circadian variability. These include, for example, metabolism and cell cycle. Similarly, many proteins that interact with pharmacological agents show variable expression during the daily cycle. The efficacy of pharmacotherapy or its toxicity may thus depend on its timing. For example, the timing of NSAIDs in osteoarthritic patients helps regulate their toxicity (Levi and Schibler 2007 [doi: 10.1146/annurev.pharmtox.47.120505.105208]), the efficacy of statins (Muck et al. 2000) and various chemotherapeutics also changes depending on time of treatment (Dakup and col. 2018 [doi: 10.18632/oncotarget.24539]). The time dependence of the effect and toxicity of radiotherapy is also known (Chan et al. 2017 [doi: 10.21037/apm.2016.09.07]). In this case, the time interval suitable for administration of the drug in terms of its maximum efficacy or minimum toxicity can often interfere with the patient's sleep or be outside the time appropriate for the healthcare professional performing the treatment. In these circumstances, it may be useful to shift the patient's internal circadian phase so that the time interval suitable for application of treatment better matches the circadian phase compatible with the maximum therapeutic outcome. A circadian rhythm modulating agent may be administered for this purpose. Accurate dosing of such an agent will allow not only to influence the period, but also to accurately time the final phase of the patient's rhythms. This or another pharmacological agent can also be used to correct the circadian phase after treatment.

SUMMARY OF THE INVENTION

The invention relates to N-(furan-2-ylmethyl)-7H-purin-6-amine (kinetin, N6-furfuryladenine) for use in treatment based on modulation of circadian rhythms in mammals, especially humans.

Circadian rhythm is an endogenous circadian rhythm of an organism or its cells, tissues and organs. Modulation of circadian rhythms includes modulation of the amplitude, period and/or phase of circadian cycle. All of these parameters are important for maintaining homeostasis, including the proper functioning of metabolism and sleep quality.

The invention is based on the finding that N-(furan-2-ylmethyl)-7H-purin-6-amine 1) modulates the activity and concentration of the molecular components of the mammalian cell circadian oscillator, and 2) modulates the period and amplitude of the circadian rhythm. In addition, by modulating the period, it is possible to achieve a phase shift of the circadian rhythm. This finding leads to a number of therapeutic applications.

A major advantage of N-(furan-2-ylmethyl)-7H-purin-6-amine over a number of bioactive compounds, including other N6-substituted purines and their biosters, is its low toxicity. Rattan and Clark (Biochem. Biophys. Res. Comm. 1994, vol. 201 (2), 665-672 [doi: 10.1006/bbrc.1994.1752]) have shown that human fibroblasts can be grown in the presence of high concentrations of this compound without any negative consequences. The compound, under the tradename Kinerase, is used in clinically tested cosmetics, and its formulation for oral administration is being evaluated as a treatment for hereditary sensory and autonomic neuropathy (clinical trial NCT02274051).

Modulation of the activity and concentration of the central molecular components of the mammalian cellular circadian oscillator influences many downstream molecular and physiological processes. These central components include clock genes, in particular the genes of the Per, Bmal, Clock, Rev-Erb, Ror and Cry families, and their protein products. Clock genes play a role in the pathogenesis of a number of diseases, including sleep disorders, cancer, myocardial infarction, and depressive disorders. Modulation of ARNTL/BMAL1 clock gene activity leads to modulation of myogenesis, adipogenesis, pancreatic beta-cell function, insulin secretion, mTOR pathway activity, chemokine expression, and hair growth. Modulation and activity of the PER2 clock gene can be used to regulate downstream processes, including the production of nitric oxide and vasodilating prostaglandins in the vessel wall, the regulation of fatty acid absorption in the liver, and the regulation of inflammatory processes.

Manipulation of the amplitude, period, and in the case of single-dose or short-term administration (<5 days) also the phase, achievable by administration of N-(furan-2-ylmethyl)-7H-purin-6-amine, is able to remedy or correct diseases, disorders and dysfunctions of circadian rhythms.

Circadian rhythm dysfunction is any deviation from the normal rhythm of a central or peripheral circadian oscillator. It also involves disrupting the physiological synchronization of individual oscillators in the body. This dysfunction may be due to abnormal function of the components of the cellular oscillators due to genetic or epigenetic errors, as well as changes in the internal environment, for example due to disease or aging.

Circadian rhythm diseases where circadian rhythm dysfunction is present include depressive disorder, unipolar depression, bipolar disorder, seasonal affective disorder, dysthymia, anxiety disorder, schizophrenia, ADHD, Alzheimer's disease, Parkinson's disease, REM-disease, Smith-Magenis syndrome, advanced sleep phase syndrome (ASPD), including its inherited form (FASPD or FASPS), delayed sleep phase syndrome, irregular and free-running sleep phase syndrome, jet lag, social jet lag, circadian dysfunction associated with shift work, hypersomnia, parasomnia, narcolepsy, nocturnal enuresis, metabolic syndrome, obesity, hyperinsulinemia, diabetes (especially type 2 diabetes), restless legs syndrome, cancer (e.g. breast, prostate, rectal cancer). N-(furan-2-ylmethyl)-7H-purin-6-amine can be administered prophylactically or therapeutically.

Modulation of abnormal circadian rhythm patterns by administration of N-(furan-2-ylmethyl)-7H-purin-6-amine can improve sleep quality. This improvement may be perceived only subjectively and may not reach a clinical stage. Sleep quality is satisfaction with the sleep experience integrating aspects of sleep initiation, sleep retention, amount of sleep, and the refreshing effect of sleep. Its reduction is the subjective feeling that some of these parameters are insufficient, or objective observation of changes in these parameters. Sleep quality can be assessed using questionnaires such as the University of Pittsburgh Sleep Quality Index (PSQI) or by measurement (actigraphy, polysomnography).

Increasing the circadian period by administration of N-(furan-2-ylmethyl)-7H-purin-6-amine has a therapeutic effect especially in diseases where the circadian cycle period is shortened and/or phase is advanced, such as in FASPS and ASPD. Long-term administration (more than 5 days) is preferred here.

Repeated administration of N-(furan-2-ylmethyl)-7H-purin-6-amine which extends the circadian period can also be used to restore or stabilize the circadian rhythm disturbed by abnormal light conditions, or by affecting parts of the CNS relevant for circadian rhythm generation that are disturbed genetically (Meng et al. 2010 [doi: 10.1073/pnas.1005101107]) or due to neurodegeneration, such as during Alzheimer's disease, Parkinson's disease and Huntington's disease.

Modulation of a period and/or phase (phase shift after a single or short-term extension of a period) by administration of N-(furan-2-ylmethyl)-7H-purin-6-amine can prevent or treat diseases and conditions caused by a person's or animal's circadian rhythm mismatch with the external environment. For prophylactic and/or therapeutic effects against jet-lag, social jet-lag, and/or shift-work disorder and sleep disorders, it is preferable to administer N-(furan-2-ylmethyl)-7H-purin-6-amine briefly (once or repeatedly for 1 to 5 days). The advantage of single and short-term administration is less burden on the body, including metabolic systems, with the drug.

Important symptoms of circadian misalignment that can be corrected by administration of N-(furan-2-ylmethyl)-7H-purin-6-amine include fatigue, worsened attention, increased reaction time, headache, memory impairment, mood disturbance, irritability, reduced manual dexterity, reduced motivation, decreased energy, or decreased initiative, nausea and sleep disturbance. A particularly important application is prevention and therapy of such symptoms in jet-lag, social-jet lag and shift-work disorder.

The symptoms of jet lag that can be corrected through normalization of circadian rhythm misalignment by administration of N-(furan-2-ylmethyl)-7H-purin-6-amine include decreased performance on mental tasks and concentration, confusion, dizziness, anxiety, irritability, increased fatigue, headache, nausea, trouble to fall asleep or remaining asleep, problems with digestion, including indigestion, alterations in the frequency of defecation and stool consistency, and reduced interest in food and its enjoyment.

The phase shift caused by a single or short-term (less than or up to 5 days) administration of N-(furan-2-ylmethyl)-7H-purin-6-amine can also be used to synchronize the optimal circadian time for veterinary or human medicine treatment in terms of its efficacy and safety with solar time appropriate for the administration of therapy in terms of the organization of the working hours of those applying therapy. In one embodiment, the treatment is tumor radiotherapy. In another embodiment, the treatment is a chemotherapy of a disease where excessive cell proliferation occurs (proliferative disease including cancer). Administration of N-(furan-2-ylmethyl)-7H-purin-6-amine may precede the administration of the therapy or may be administered simultaneously with the therapy. Examples of suitable agents for combination with N-(furan-2-ylmethyl)-7H-purin-6-amine include agents that damage DNA and/or inhibit cell cycle passage. Particularly suitable compounds are, for example, melphalan, busulfan, mitoxanthrone, cyclophosphamide, ifosfamide, carmustine, lomustine, bendamustine, uramustine, cisplatin, carboplatin, oxaliplatin, dacarbazine, mitozolomide, temizolomide, ribociclib, palbociclib, abemaciclib, vincristine, vinblastine, vinorelbine, docetaxel, paclitaxel, ixabepilone, irinotecan and topotecan. There is sufficient evidence that the patient's response to therapy depends on the phase of his endogenous circadian clock, and so-called chronotherapy currently receives considerable attention (Dakup et al. 2018 [doi: 10.18632/oncotarget.24539], Okyar et al. 2010 [doi: 10.1146/annurev.pharmtox.48.113006.094626], Chan et al., 2016 [doi: 10.21037/apm.2016.09.07], Zaki et al., 2019 [doi: 10.1021/bi5007354]).

The invention also provides N-(furan-2-ylmethyl)-7H-purin-6-amine for use in modulating the response of mammals, including humans, and their cells, tissues and organs (in vitro or in vivo) to stimuli affecting circadian rhythms. N-(furan-2-ylmethyl)-7H-purin-6-amine and the appropriate stimulus may be administered simultaneously, for example in the form of a combined preparation (if the stimulus is a chemical), or sequentially.

In one embodiment, the stimulus may be light, including artificial light and including various light therapy modalities. The combination of N-(furan-2-ylmethyl)-7H-purin-6-amine and light has a beneficial effect on sleep and mood disorders, including Advance Sleep Syndrome (ASPD), its age-related forms and its and its hereditary form (FASPS), irregular sleep phase and free-running sleep syndrome, jet-lag, social jet-lag, shift work-related circadian dysfunction, depressive disorders, unipolar depression, bipolar disorder, seasonal affective disorders, dementia and Parkinson's disease.

In another embodiment, the stimulus is another chronotherapeutic. A chronotherapeutic is a compound that modulates the circadian rhythm or changes its sensitivity to entrainment.

In a preferred embodiment, the invention includes a combination of N-(furan-2-ylmethyl)-7H-purin-6-amine and a chronotherapeutic selected from the group consisting of: CSNK1D inhibitors, CSNK1A inhibitors, CSNK1E inhibitors, GSKbeta inhibitors, ALK5 inhibitors, AMPK activators, activators SIRT1, CRY ligands, PPARG agonists, BMAL1 expression regulators, vasopressin receptor ligands, REV-ERB agonists, RORα/γ agonists. Preferably, the additional chronotherapeutic is selected from the group consisting of melatonin receptor agonists including melatonin, ramelteon, tasimelteon and agomelatine. These combinations usually have an additive or synergistic effect on the period and/or phase, but the addition of kinetin may also change the amplitude. In some cases, such as in combination with the chronotherapeutic harmine, the addition of kinetin shortens the period compared to the condition when harmine alone is used. Thus, kinetin can be used to precisely modulate the effect of other chronotherapeutics.

This invention also provides preparations containing a combination of N-(furan-2-ylmethyl)-7H-purin-6-amine and at least one other chronotherapeutic in concentrations effective for prophylactic or therapeutic modulation of circadian rhythms and/or sleep of mammals including humans.

This invention also provides preparations containing combination of N-(furan-2-ylmethyl)-7H-purin-6-amine and at least one antineoplastic.

N-(furan-2-ylmethyl)-7H-purin-6-amine and the other active ingredient (chronotherapeutic or cytostatic) may be used as described herein and/or present in the compositions in the form of pharmaceutically acceptable salts or solvates. Pharmaceutically acceptable salts of N-(furan-2-ylmethyl)-7H-purin-6-amine are formed by protonation of one of the nitrogens with an inorganic or organic acid. Examples of salts with inorganic acids include hydrochlorides, hydrobromides, hydroiodides, sulfates, nitrates, phosphates, hydrogen phosphates, dihydrogen phosphates, carbonates, bicarbonates, perchlorates. Examples of salts with organic acids include salts with straight or branched chain polyhydric or polybasic acids having 2 to 20 carbons, such as lactate, maleate, oxalate, fumarate, tartrate, malate, maleate, citrate, succinate, glycolate, nicotinate, benzoate, salicylate, ascorbate, pamoate; sulfonate, methanesulfonate, ethanesulfonate, 2-hydroxyethanesulfonate, benzenesulfonate, p-toluenesulfonate, 2-naphthalenesulfonate, 3-phenylsulfonate and camphorsulfonate, aspartate or glutamate.

Combined pharmaceutical preparations for co-administration contain an effective amount of N-(furan-2-ylmethyl)-7H-purin-6-amine and other active ingredients (chronotherapeutics or cytostatics), or pharmaceutically acceptable salts or other forms thereof, alone or in combination. Mixtures with one or more excipients such as carriers, fillers, solvents, tablet degradants, lubricants, integrity enhancers, pigments, stabilizers, preservatives, antioxidants, solubility enhancers. The preparation may contain excipients that increase penetration through biological barriers, for example through the skin. However, in addition to co-administration, the active ingredients may be administered alone (sequentially) at intervals. In that case, each of these active ingredients is contained in a separate dosage form, usually together with one or more excipients.

In a preferred embodiment, these preparations are in the dosage form for oral administration. Only in case of antineoplastics administered as an infusion, infusion form is preferred. In another important embodiment, the dosage forms are for transdermal, inhalation or nasal administration. In other embodiments, the dosage forms are for other modes of parenteral administration, such as intravenous, intramuscular, subcutaneous, or topical administration.

Dosage forms for oral administration include coated and uncoated tablets, soft and hard gelatin capsules, matrix tablets, solutions, emulsions, suspensions, syrups, powders and granules for reconstitution, chewable and effervescent tablets. Dosage forms for parenteral administration include solutions, emulsions, suspensions and dispersions, powders and granules for reconstitution. Other contemplated dosage forms include suppositories, transdermal penetration dosage forms, implants, and insufflation and inhalation dosage forms. Topical dosage forms include creams, gels, ointments and patches.

EXAMPLES OF CARRYING OUT THE INVENTION

Example 1: N-(furan-2-ylmethyl)-7H-purin-6-amine Prolongs the Circadian Rhythm Period of Human Cells Human osteosarcoma U2OS cells were grown in standard DMEM with 10% fetal calf serum. U2OS cells were transduced with lentiviral particles containing the reporter pLV6-Bmal1-Luc (S. Brown, Addgene plasmid #68833) and selected under Blasticidin. The cell line was clonally expanded and a single monoclonal cell line was used for further experiments. Cells were cultured in a 384-well plate in growth medium to 90+% confluence. Test compound or vehicle (DMSO) was applied to recording medium with 100 U/ml penicillin, 100 µg/ml streptomycin, 1× GlutaMAX (ThermoFisher, Waltham, MA, USA), 10% fetal calf serum (Sigma) and 0.1 mM Luciferin-EF (Promega Madison, WI, USA).

Figure 1:
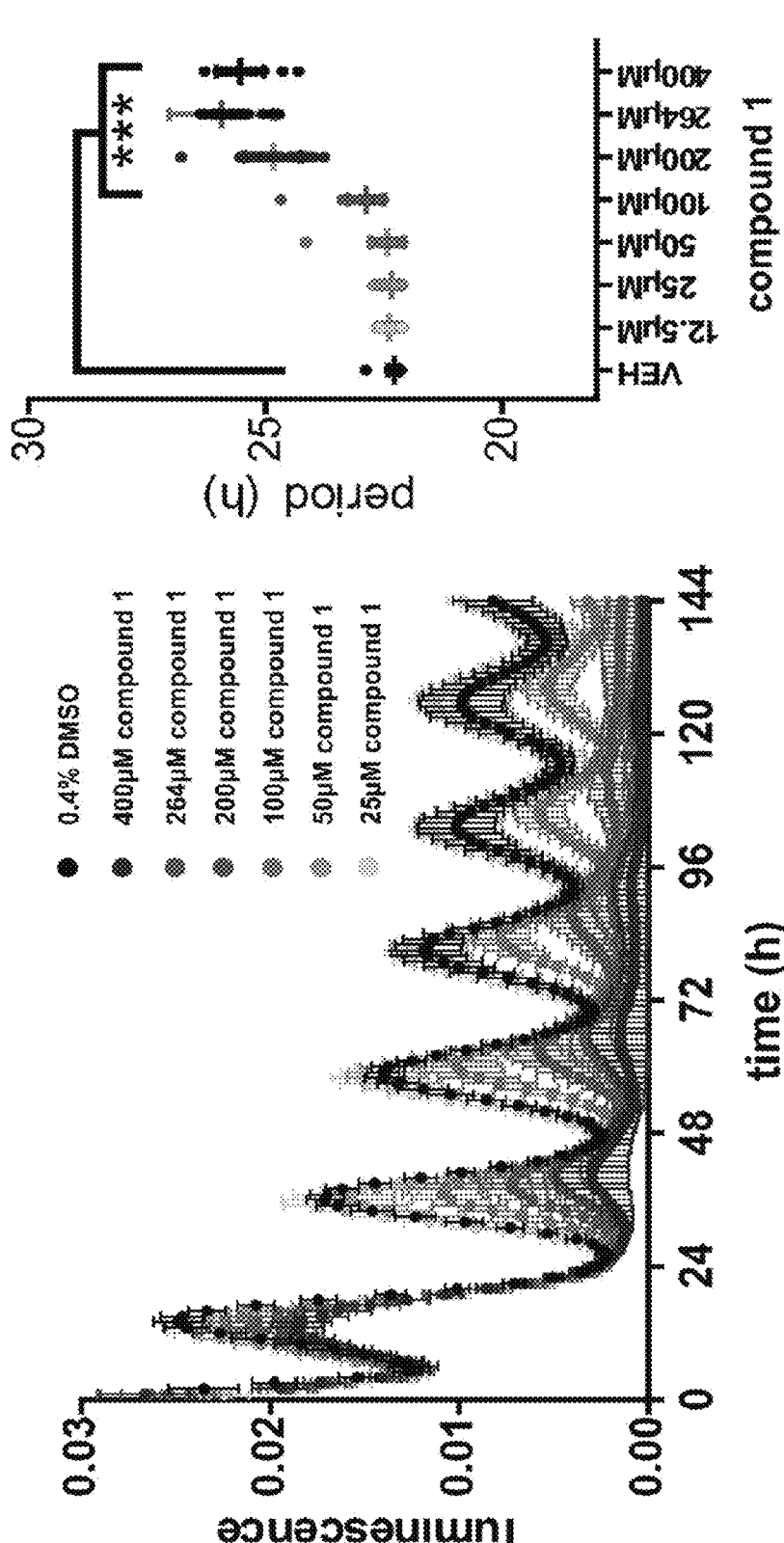
FIG. 1: N-(furan-2-ylmethyl)-7H-purin-6-amine (compound 1) regulates the expression of Bmal1 gene and increases the period of the circadian rhythm of human cells U2OS transduced by transcriptional circadian reporter mBmal1-Luc (Example 1).

Luminescence was recorded every hour for an additional 144 hours in Luminoskan Ascent (ThermoFisher). Circadian rhythm analysis was performed using cosinor analysis. The results are shown in FIG. 1.

This experiment demonstrates that N-(furan-2-ylmethyl)-7H-purin-6-amine extends the circadian rhythm period of human cells and can be used to manipulate the circadian rhythm phase, for example, to synchronize the endogenous circadian clock with solar time. The overall effect on circadian oscillations indirectly but unequivocally demonstrates that N-(furan-2-ylmethyl)-7H-purin-6-amine can also be used to modulate the concentration and activity of other oscillator components, including the critical components BMAL1, PER2, CRY and CLOCK over time, as these are an essential part of the mechanism for generating rhythmic expression of the used luminescent reporter. The concentration and level of other proteins, whose rhythmic expression is controlled by an oscillator in the brain and peripheral tissues (so-called clock-controlled genes), is also necessarily affected. The effect of N-(furan-2-ylmethyl)-7H-purin-6-amine on the activity of oscillator components and subordinate genes also means influencing the physiological processes of the cell controlled by these genes and proteins.

Figure 2:
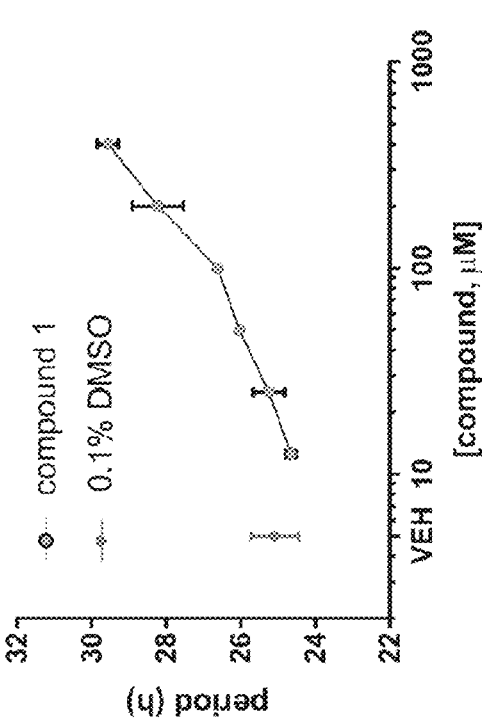
FIG. 2: N-(furan-2-ylmethyl)-7H-purin-6-amine (compound 1) increases the period and modulates the amplitude of circadian expression of transcriptional clock reporter mPer2-Luc in mouse cells NIH3T3 (Example 2).
Figure 2:
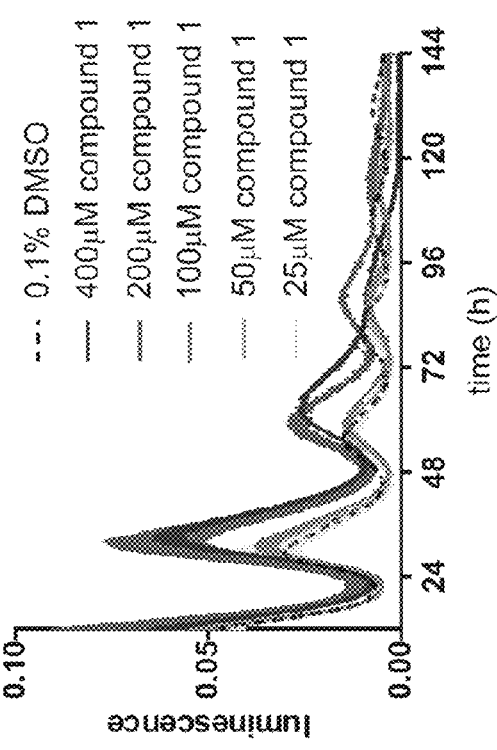

Example 2: N-(furan-2-ylmethyl)-7H-purin-6-amine Prolongs the Circadian Rhythm Period of Mouse Cells Mouse embryonic fibroblasts NIH3T3 cells were grown in standard DMEM with 10% fetal calf serum. NIH3T3 cells were transfected with 1 µg of Per2-Luc reporter (Meng, 2009) using GeneJuice (Novagen) and selected under hygromycin. The cell line was clonally expanded and a single monoclonal cell line was used for further experiments. Cells were cultured in a 96-well plate in growth medium to 90+% confluence. Test compound or vehicle (DMSO) was applied to recording medium with 100 U/ml penicillin, 100 µg/ml streptomycin, 1×GlutaMAX (ThermoFisher, Waltham, MA, USA), 10% fetal calf serum (Sigma) and 0.1 mM Luciferin-EF (Promega Madison, WI, USA). Luminescence was recorded every hour for an additional 144 hours in a Luminoskan Ascent (ThermoFisher). Circadian rhythm analysis was performed using cosinor analysis. The results are shown in FIG. 2. The experiment demonstrates that N-(furan-2-ylmethyl)-7H-purin-6-amine prolongs the circadian rhythm period of mouse cells and can be used to manipulate the circadian rhythm phase, for example, to synchronize the internal circadian clock with solar time. The overall effect on circadian oscillations indirectly, but unequivocally, demonstrates that N-(furan-2-ylmethyl)-7H-purin-6-amine can also be used to modulate the concentration and activity of other oscillator components, including the critical components Bmal1, Per2, Cry and Clock, as these are an essential part of the mechanism for generating the rhythmic expression of the luminescent reporter used. The concentration and level of other proteins, whose rhythmic expression is controlled by an oscillator in the brain and peripheral tissues (so-called clock-controlled genes), is also necessarily affected. The effect of N-(furan-2-ylmethyl)-7H-purin-6-amine on the activity of oscillator components and subordinate genes also means influencing the physiological processes of the cell by these genes and proteins controlled.

Example 3: N-(furan-2-ylmethyl)-7H-purin-6-amine Prolongs the Period and Modulates the amplitude of circadian expression of the PER2::Luc clock reporter in the explanted suprachiasmatic nuclei (SCN) of the hypothalamus, the central clock of mammals, of the transgenic mouse line Male and female mPer2Luc mice (strain B6.129S6-Per2tm1Jt/J, JAX, USA) (Yoo et al., 2004) were maintained in a light/dark cycle with 12 hours of light and 12 hours of darkness (LD12: 12), killed between 12:00 and 15:00, i.e. 6-9 hours after turning on the lights, by rapid cervical dislocation under isoflurane anesthesia, their brains were removed and 250 µm thick SCN slices in ice-cold HBSS medium were prepared using a vibratome (Leica, Wetzlar, Germany). Two explants containing SCN from each brain were prepared. Individual SCN explants were then placed on Millicell Culture Inserts (Merck, Darmstadt, Germany) inside 35 mm Petri dishes with test compound or DMSO vehicle in 1 ml air-buffered recording medium supplemented with 100 U/ml penicillin, 100 µg/ml streptomycin (Sigma-Aldrich, St. Luis, MO, USA), 1×GlutaMAX (ThermoFisher, Waltham, MA, USA), 5% fetal calf serum (Sigma) and 0.1 mM Luciferin-EF (Promega Madison, WI, USA). The dishes were sealed with vacuum Vaseline and glass coverslips and placed inside a LumiCycle (Actimetrics) for bioluminescence recording. Rhythm analysis was performed in Lumicycle Analysis software (Actimetrics).

Figures 3A, 3B, 3C:
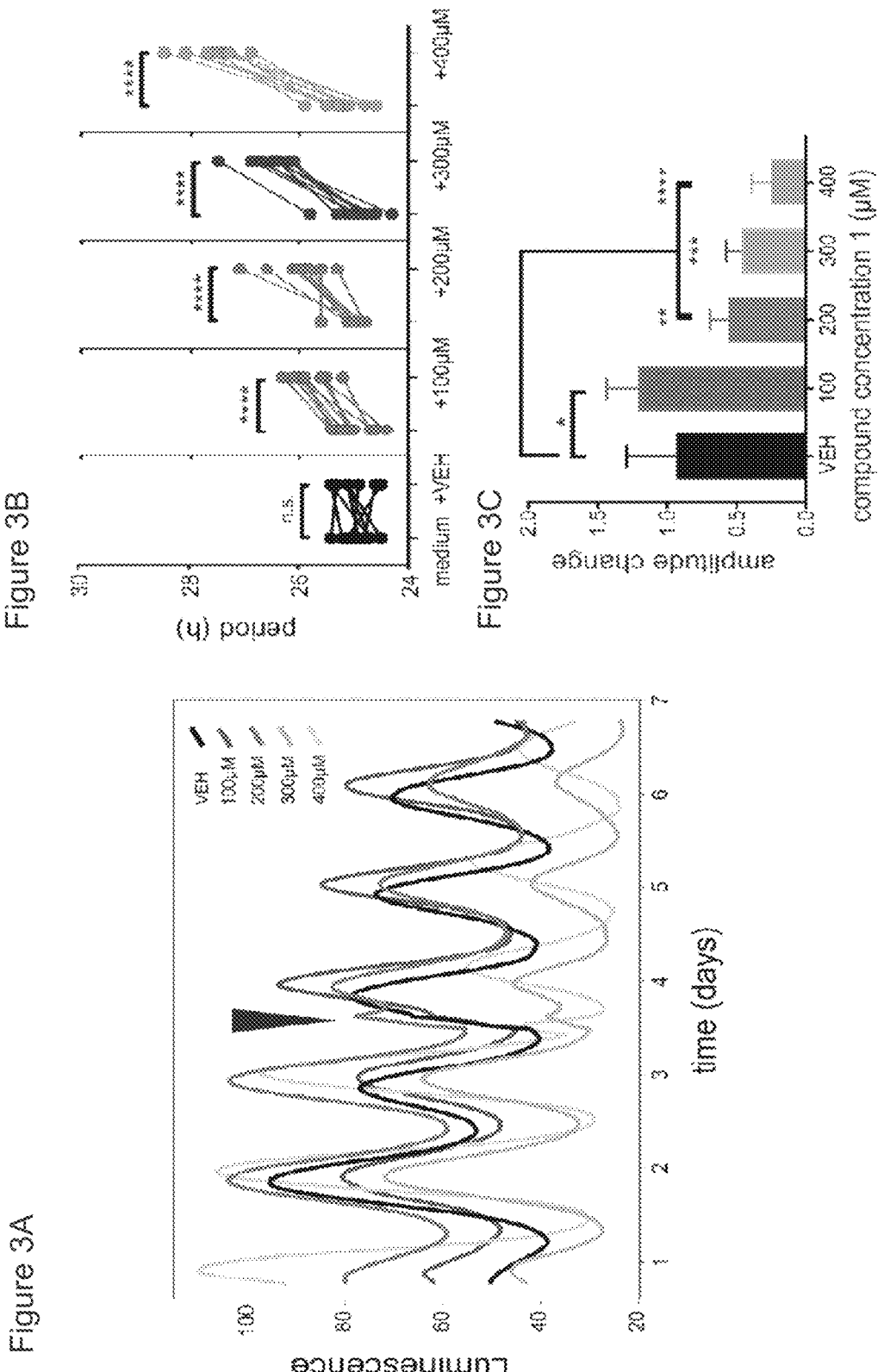
FIGS. 3A-3C: N-(furan-2-ylmethyl)-7H-purin-6-amine (compound 1) increases the period and modulates the amplitude in organotypic explants of hypothalamic suprachiasmatic nucleus (SCN). Representative luminescence recordings directly show PER2 protein levels, black arrows indicate the time when the compound was added to the medium (FIG. 3A). The circadian period (FIG. 3B) and amplitude (FIG. 3C) after application of the compound in the given* concentration. (Example 3).

The results are shown in FIGS. 3A-3C.

The example demonstrates that N-(furan-2-ylmethyl)-7H-purin-6-amine prolongs the circadian rhythm period and modulates the period in the complex tissue of the central pacemaker and can be used to manipulate the circadian rhythm phase, for example to synchronize the internal circadian clock with solar time. The overall effect on the circadian oscillator indirectly, but unequivocally, demonstrates that the compound can also be used to modulate the concentration and activity of other components of the oscillator, including the critical components Bmal, Per2, Cry and Clock over time. The concentration and level of other proteins, whose rhythmic expression is controlled by an oscillator in the brain and peripheral tissues (so-called clock-controlled genes), is also necessarily affected. The effect of N-(furan-2-ylmethyl)-7H-purin-6-amine on the activity of the oscillator components and subordinate genes also means influencing the physiological processes of the cell controlled by these genes and proteins.

Figure 4:
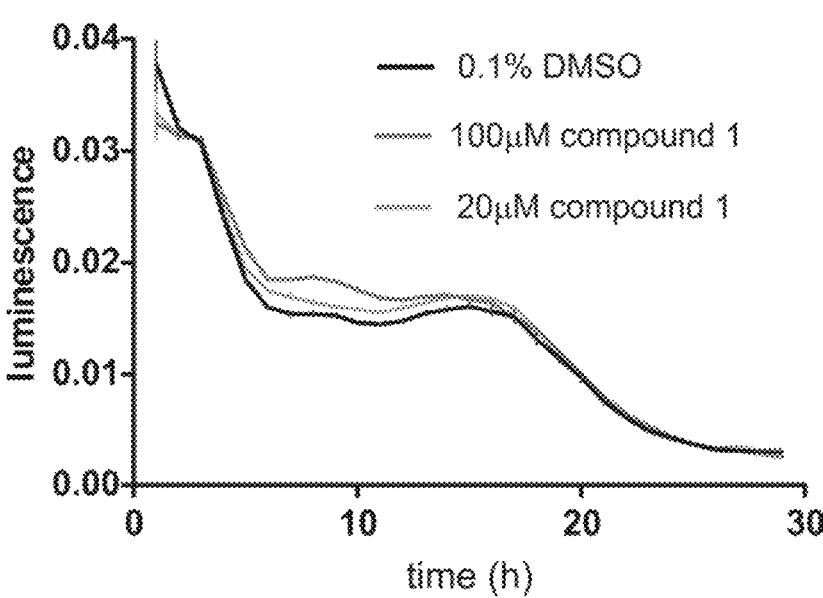
FIG. 4: N-(furan-2-ylmethyl)-7H-purin-6-amine (compound 1) modulates the expression of mBmal1-Luc reporter during the first 5-15 hours after the application into the medium. (Example 4).
Figure 5:
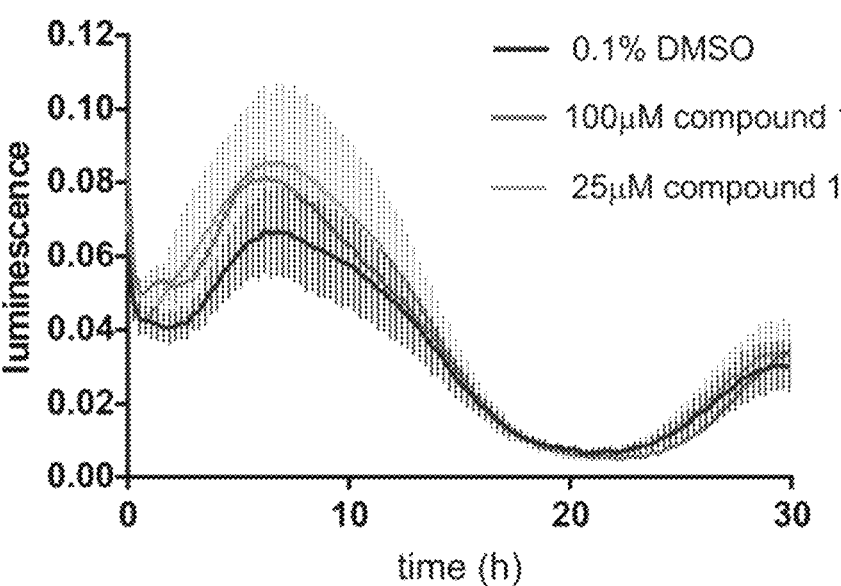
FIG. 5: N-(furan-2-ylmethyl)-7H-purin-6-amine (compound 1) modulates the expression of mPer2-Luc reporter during the first 1-12 hours after the application into the medium. (Example 5).
Figures 6A, 6B, 6C, 6D, 6E, 6F:
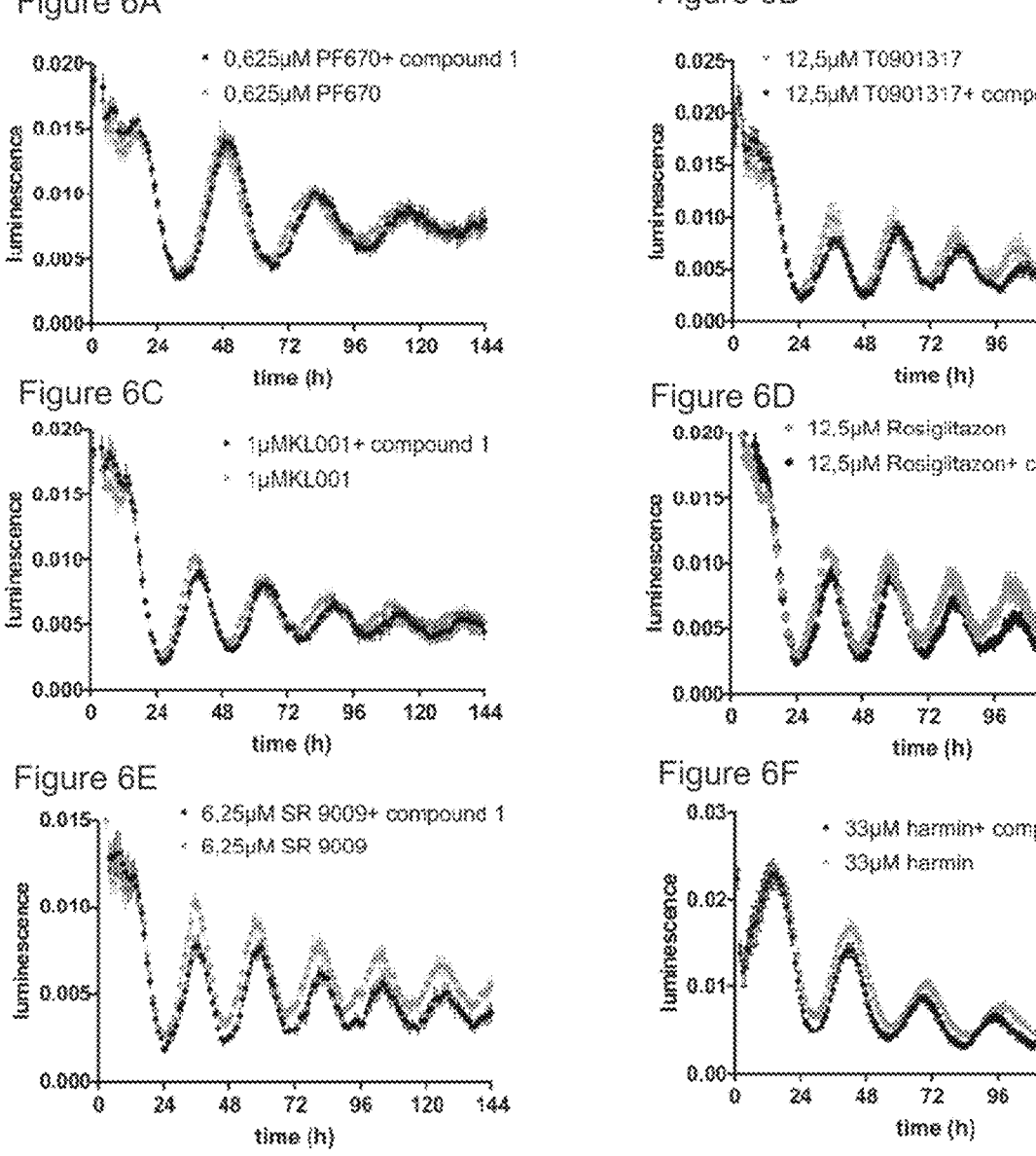
FIGS. 6A-6F: N-(furan-2-ylmethyl)-7H-purin-6-amine (compound 1) modulates the effect of other chronotherapeutics on the expression of mBmal1-Luc reporter in U2OS cells. In the medium, a compound modulating circadian rhythm was present together with N-(furan-2-ylmethyl)-7H-purin-6-amine (50 µM, black line) or equivalent amount of DMSO vehicle (gray). Depending on the type of the added compound, an additive (FIG. 6A) or synergistic (FIG. 6B, 6C, 6D, 6E) effect on the period increase was observed. In the case of harmine (FIG. 6F), the addition of N-(furan-2-ylmethyl)-7H-purin-6-amine caused a decrease of the period. Mechanisms of the compounds' actions were as follows: PF670 (PF-670462)—non-selective CK1d/e inhibitor; T0901317—ROR agonist; KL001—CRY1 degradation inhibitor; rosiglitazon—PPARG agonist, SR9009—REVERBa/b agonist; harmin—DYRK1 inhibitor and modulator of BMAL1 transcription (Example 6).

Example 4: N-(furan-2-ylmethyl)-7H-purin-6-amine Modulates the Expression of the Bmal1 Gene and Protein Human osteosarcoma U2OS cells were grown in standard DMEM with 10% fetal calf serum. U2OS cells were transduced with lentiviral particles containing the reporter pLV6-Bmal1-Luc (S. Brown, Addgene plasmid #68833) and selected under Blasticidin. The cell line was clonally expanded and a single monoclonal cell line was used for further experiments. Cells were cultured in a 384-well plate in growth medium to 90+% confluence. Test compound or vehicle (DMSO) was applied to recording medium with 100 U/ml penicillin, 100 µg/ml streptomycin, 1×GlutaMAX (ThermoFisher, Waltham, MA, USA), 10% fetal calf serum (Sigma) and 0.1 mM Luciferin-EF (Promega Madison, WI, USA). Luminescence was recorded every hour for additional 144 hours in Luminoskan Ascent (ThermoFisher). The results are shown in FIG. 4.

The example demonstrates that N-(furan-2-ylmethyl)-7H-purin-6-amine affects Bmal1 gene expression in human cells. A change in the level of Bmal1 mRNA affects its protein level. Because this protein controls the expression of other circadian oscillator genes and directly activates the expression of a number of other genes containing the E-box in their regulatory DNA region and exhibiting circadian oscillations, N-(furan-2-ylmethyl)-7H-purin-6-amine also affects their expression.

Example 5: N-(furan-2-ylmethyl)-7H-purin-6-amine Regulates Per2 Gene and Protein Expression Mouse embryonic fibroblasts NIH3T3 cells were grown in standard DMEM with 10% fetal calf serum. NIH3T3 cells were transfected with 1 µg of Per2-Luc reporter (Meng, 2009) using GeneJuice (Novagen) and selected under hygromycin. The cell line was clonally expanded and a single monoclonal cell line was used for further experiments. Cells were cultured in a 96-well plate in growth medium to 90+% confluence. Test compound or vehicle (DMSO) was applied to recording medium with 100 U/ml penicillin, 100 µg/ml streptomycin, 1×GlutaMAX (ThermoFisher, Waltham, MA, USA), 10% fetal calf serum (Sigma) and 0.1 mM Luciferin-EF (Promega Madison, WI, USA). Luminescence was recorded every hour for additional 144 hours in Luminoskan Ascent (ThermoFisher). The results are shown in FIG. 4.

The example demonstrates that N-(furan-2-ylmethyl)-7H-purin-6-amine regulates Per2 gene expression in mouse cells. The change in the mRNA level also affects the level of the PER2 protein. Because this protein controls the expression of other circadian oscillator genes and inhibits the expression of a number of other genes exhibiting circadian oscillations, N-(furan-2-ylmethyl)-7H-purin-6-amine also affects their expression.

Example 6: N-(furan-2-ylmethyl)-7H-purin-6-amine modulates the Response of Cells to Other Stimuli Affecting Circadian Rhythm Human osteosarcoma U2OS cells were grown in standard DMEM with 10% fetal calf serum. U2OS cells were transduced with lentiviral particles containing the reporter pLV6-Bmal1-Luc (S. Brown, Addgene plasmid #68833) and selected under Blasticidin. The cell line was clonally expanded and a single monoclonal cell line was used for further experiments. Cells were cultured in a 384-well plate in growth medium to 90+% confluence. Test compounds or vehicle (DMSO) were applied to recording medium with 100 U/ml penicillin, 100 µg/ml streptomycin, 1×GlutaMAX (ThermoFisher, Waltham, MA, USA), 10% fetal calf serum (Sigma) and 0.1 mM Luciferin-EF (Promega Madison, WI, USA). Luminescence was recorded every hour for additional 144 hours in Luminoskan Ascent (ThermoFisher). Circadian rhythm analysis was performed by cosinor analysis.

The example demonstrates that N-(furan-2-ylmethyl)-7H-purin-6-amine in combination with compounds that extend the circadian period by different mechanisms of action has an additive or even synergistic effect on the length of the circadian period in human cells and can be used to enhance the effect of these compounds. Conversely, depending on the mechanism of action, some compounds (in this case, harmine) shorten the period after the addition of N-furan-2-ylmethyl)-7H-purin-6-amine, so it can be used to negatively modulate the effect of this type of compound.

Example 7: N-(furan-2-ylmethyl)-7H-purin-6-amine Sensitize Cancer Cells to Antineoplastics Resazurin is a blue weakly fluorescent compound that is irreversibly reduced into red highly fluorescent resofurin by metabolically active cells and can be therefore used for viability tests. In this assay, the effect of antineoplastics on viability of cancer cell line A549 pretreated with N-(furan-2-ylmethyl)-7H-purin-6-amine (final concentration 100 micromol) was evaluated.

Figure 7:
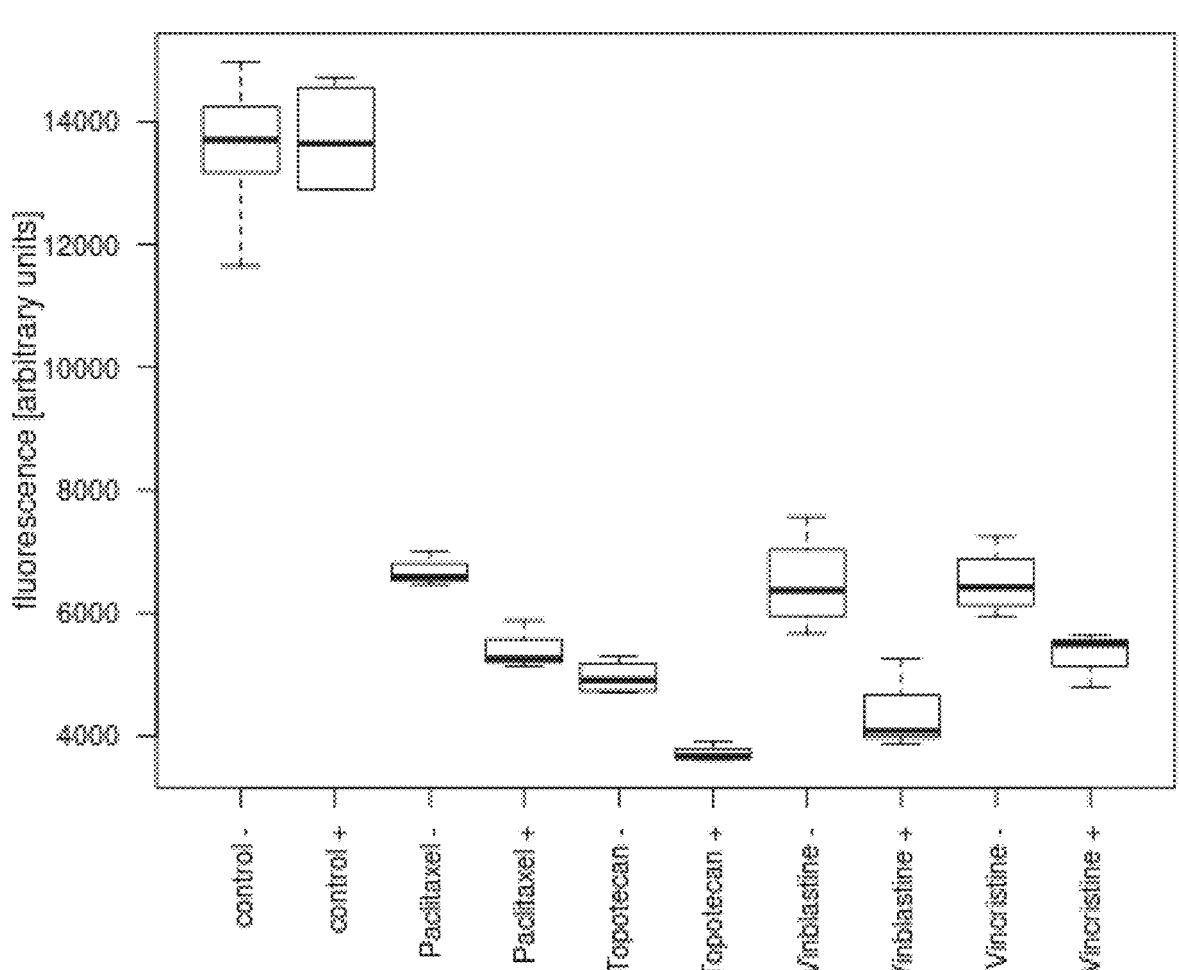
FIG. 7: Effect of the combination of N-(furan-2-ylmethyl)-7H-purin-6-amine (+) or DMSO vehicle (−) with antineoplastics on the viability of the cancer cell line A549 (Example 7).

Human cancer cell line A549 was maintained in standard cultivation medium DMEM with 10% fetal bovine serum. 1000 cells were seeded into the wells of 384-well plate in 30 microliters of RPMI medium. After 24 hours, dexamethasone (final concentration 100 nM) was added in order to synchronize circadian oscillator together with N-(furan-2-ylmethyl)-7H-purin-6-amin (final concentration 100 µM) or DMSO vehicle. After 12 hours, DMSO vehicle or the evaluated antineoplastics (the final concentration 3.3 µM)

were added. The compounds were dosed by ECHO system, the DMSO solutions were 1000-times concentrated. After 72 incubation, 1000-times concentrated solution of resazurin in DMSO to a final concentration of 0.0125 mg/ml was added. Fluorescence was measured after 3-hour incubation. Results are shown in FIG. 7. It was demonstrated that pretreatment with N-(furan-2-ylmethyl)-7H-purin-6-amine increases activity of antineoplastics. An equivalent cytotoxic effect can be therefore achieved by an application of lower dose of antineoplastics.

Example 8: N-(furan-2-ylmethyl)-7H-purin-6-amine is not Toxic for Human Non-Cancer Cell Lines in Resazurin Test Resazurin is a blue weakly fluorescent compound that is irreversibly reduced into red highly fluorescent resofurin by mitochondria. It is used for viability testing of eukaryotic cells. The effect of the compounds in several concentrations (maximum concentration of 100 microM and 3 three-fold dilutions) on viability of skin fibroblasts BJ and retinal epithelium cells ARPE-19 was evaluated after 72 hour treatment. The cells were maintained in standard cultivation medium DMEM with 10% fetal bovine serum. 5000 cells were seeded into 96-well plates 24 hours prior to the addition of test compound. DMSO vehicle was used as a negative control. After 72 hours, 1000-times concentrated solution of resazurin in DMSO was added to the cells zo the final concentration of 0.0125 mg/ml. Fluorescence (ex=570 nm, em=610 nm) was measured after 1 hour (ARPE-19) or 3 hours (BJ) of incubation. IC50 values were calculated from dose response curves using drc library for R programming environment.

Following results were obtained: Resazurin test after 3 day exposure-ARPE-19 $IC_{10}$>100 µM and BJ $IC_{10}$>100 microM. N-(furan-2-ylmethyl)-7H-purin-6-amine has a favorable toxicity profile for human non-cancer cells. This is an important advantage in comparison with many other N6-substituted purines and their biosters many of which are toxic sometimes because of the inhibition of cyclin dependent kinases (Voller et al. 2010 [doi: 10.1016/j.phytochem.2010.04.018], Jorda et al. 2012 [doi: 10.2174/138161212800672804]).

Figure 8:
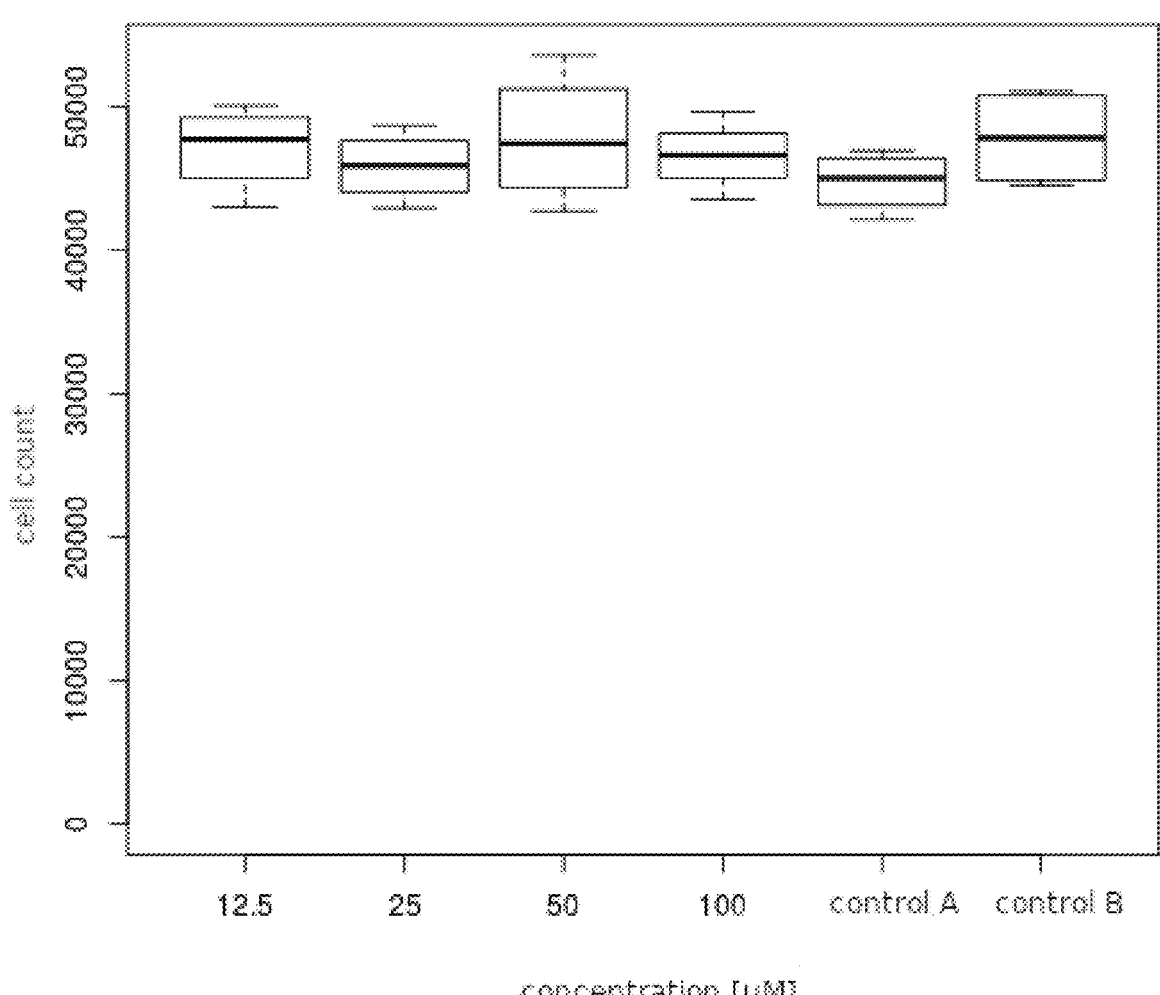
FIG. 8: Effect of N-(furan-2-ylmethyl)-7H-purin-6-amine on the BJ fibroblasts growth. The cell count in the wells of a 24-well plates after 12 days (Example 9).

Example 9: N-(furan-2-ylmethyl)-7H-purin-6-amine is not Toxic for Normal Human Cell During a Long-Term Cultivation Human fibroblasts BJ were maintained in standard cultivation medium DMEM with 10% fetal bovine serum. The experiment was performed in 24-well plates. 10,000 cells in DMEM medium with 10% fetal bovine serum were seeded into the wells. The test compound was added to a final concentration in the range of 12.5-100 UM after 24 hours. DMSO vehicle was used as a negative control. In order to obtained better idea of test variability, 8 control wells were used (columns A and D). The cultivation medium containing either test compound or DMSO was replaced twice a week. The cells were trypsinized on the 12th day and counted on Coulter Z2 apparatus. The test compound in the evaluated concentration range and exposure time did not have a negative effect on cell growth. The results are shown in FIG. 8.

N-(furan-2-ylmethyl)-7H-purin-6-amine has a favorable toxicity profile in human noncancer cells. This is an important advantage in comparison with many other N6-substituted purines and their biosters many of which are toxic sometimes because of the inhibition of cyclin dependent kinases (Voller et al. 2010 [doi: 10.1016/j.phytochem.2010.04.018], Jorda et al. 2012 [doi: 10.2174/138161212800672804]).

Example 10:
N-(furan-2-ylmethyl)-7H-purin-6-amine has Favorable Pharmacokinetic Parameters Analytical Chemistry Quantification of N-(furan-2-ylmethyl)-7H-purin-6-amine in the samples was performed using RapidFire RF300 system (Agilent Technologies) interfaced with QTRAP 5500 mass spectrometer fitted with an electrospray ionization source (AB Sciex, Concord, Canada) and running in multiple-reaction monitoring mode.

This system is further referred to as RF-MS. Preparation of the lyophilized samples for the analysis is described in the sections dedicated to the individual methods. Lyophilized samples were dissolved in the mobile phase (95% water, 5% acetonitrile, 0.1% formic acid) with respective internal standards. The dissolved samples were aspirated directly from 96-well plates into a 10 µL sample loop and passed through a C4 cartridge (Agilent Technologies) with solvent A (95% water, 0.01% formic acid, 5% acetonitrile) at a flow rate of 1.5 mL/minute for 3 seconds. After the desalting step, the analyte retained on the cartridge was eluted with solvent B (95% acetonitrile, 5% 0.01% formic acid) to the mass spectrometer at a flow rate of 0.4 mL/minute for 7 seconds. Mass spectrometry was carried out using electrospray ionization in the positive ion mode. Daughter ion peaks were identified using a multiple-reaction monitoring protocol.

Evaluation of Stability in Human Plasma

Test compound (a final concentration of 2 µM) was incubated with human plasma (Transfusion Department, University Hospital Olomouc, Olomouc, Czech Republic) for 0, 15, 30, 60 and 120 min at 37° C. The reactions were stopped by addition of acetonitrile-methanol mixture (2:1). Samples were stored at –80° C. overnight and centrifuged (2811×g, 6 min, 4° C.). Supernatants were lyophilized.

Evaluation of Microsomal Stability

The reaction mixtures of test compounds (2 M), human liver microsomes (ThermoFisher Scientific, 0.5 mg/mL), NADPH generating system (NADP+-0.5 mM, isocitrate dehydrogenase-6 U/mL, isocitric acid—4 mM, and MgSO$_4$—5 mM) in 0.1 mol/L K$_3$PO$_4$ buffer. The reactions were stopped by the addition of acetonitrile-methanol mixture (2:1) after 0, 15, 30, and 60 min at 37° C. The samples were centrifuged (2811×g, 6 min, 4° C.) and the supernatants were lyophilized.

Calculations: The intrinsic clearance was calculated as $CL_{int}=V^*(0.693/t_{1/2})$, where V is the volume of the reaction in µL related to the weight of the microsomal protein in mg per reaction. Elimination half-life was calculated using the equation $t_{1/2}=0.693/k$, where k is the slope of linear regression of natural logarithm of percent substrate remaining plotted versus incubation time.

Evaluation of Permeability Through Passive Diffusion—PAMPA

The parallel artificial membrane permeability assay (PAMPA) was performed using the Millipore MultiScreen filter MultiScreen-IP Durapore 0.45 µm plates and receiver plates (Merck Millipore) according to the manufacturer's protocol PC040EN00. The test compounds were dissolved in PBS (pH 7.4) to the final concentration of 20 AM and added to the donor wells. The filter membrane was coated with 10% lecithin (Sigma Aldrich) dissolved in dodecane and the acceptor wells were filled with PBS (pH 7.4). The acceptor filter plate was carefully placed on the donor plate. Following 18-hour incubation at the room temperature aliquots of acceptor and donor solutions were removed and lyophilized.

Calculations: The relative permeability log Pe was calculated as log Pe=log{Cx−ln(1−drug$_A$/drug$_E$)}, where $C=(V_A×V_D)/\{(V_D+V_A)×A×T\}$. $V_D$ and $V_A$ are the volumes of the donor and acceptor solutions, respectively, A is the active surface area in cm$^2$ and T is time of the incubation in seconds. DrugA and drugE is the mass of the compound in the acceptor solution and in the solution in theoretical equilibrium (as if the donor and acceptor were combined), respectively.

Evaluation of Plasma Protein Binding

The assay is based on the rapid equilibrium dialysis (RED). The RED plate inserts (Thermo Scientific™, Rockford, USA) consist of two chambers separated by a semipermeable membrane. For each compound, 10 µM in 10% human plasma was transferred into the one chamber and the other was filled with PBS buffer (pH 7.4). The equal volumes of the solutions from either compartment were transferred into microtubes after the 4-hour incubation with shaking (250 rpm). Either 10% plasma or PBS buffer (pH 7.4) was added so that all the samples had the same matrix. The reactions were stopped by the addition of acetonitrile-methanol mixture (2:1). The samples were centrifuged (2811×g, 6 min, 4° C.) and the supernatants were lyophilized.

Evaluation of Transport Across Caco-2 and MDR-MDCK Monolayers

Caco-2 (American Tissue Type Collection) a MDR1-MCDK (Netherlands Cancer Institute) were cultured in DMEM medium with 10% fetal bovine serum. In order to generate cell monolayers for transport studies, the cells were trypsinized and seeded on tissue culture polyester membrane filters (pore size 0.4 µm for Caco-2 and 1 µm for MDR1-MCDK) in 96-well Transwell® plates (Corning, NY, USA). The culture medium was added to both the donor and the acceptor compartments and the cells were allowed to differentiate and form the monolayers. The culture medium was changed every other day.

Caco-2 and MDR1-MCDK differentiated monolayers were used only if they were intact, which was confirmed by Lucifer Yellow Rejection Assay. Prior to the experiment, the cells were washed twice with Hank's balanced buffer solution (HBBS) (Gibco, Waltham, USA) and pre-equilibrated with HBSS buffer at pH 7.4 for 1 h. After removing the medium, the cells were treated with 10 µM test compounds in HBSS (pH 7.4) for 1 and 2 h, for MDCK and Caco-2, respectively. Thereafter, the samples were removed from both donor and acceptor compartments and lyophilized. All experiments were done in duplicate.

Calculations: The apparent permeability coefficient was calculated as $P_{app}=(dQ/dt)/(C_0×A)$, where dQ/dt is the rate of permeation of the drug across the cell monolayer, $C_0$ is the donor compartment concentration at time t=0 and A is the area of the cell monolayer. The efflux ratio R was defined as ratio $P_{BA}/P_{AB}$ where $P_{BA}$ and/$P_{AB}$ represent the apparent permeability of test compound from the basal to apical and apical to basal side of cell monolayer, respectively. The compounds with the efflux ratio of 2 or higher were considered as potential P-gp substrates.

TABLE 1

The results of the panel of in vitro pharmacokinetics tests.
Values $P_{app}$ >20 × $10^{-6}$ for Caco-2 and $P_{app}$ >10 × $10^{-6}$ for MDR-MDCK indicate good oral and CNS bioavailability, respectively.

| MDR1-MDCK permeability $(P_{app} \times 10^{-6})$/ | Caco-2 permeability $(P_{app} \times 10^{-6})$ | PAMPA permeability (log $P_e$) | Mikrosomal stability (60 min) [% intact] | Plasma stability (120 min) [% intact] |
|---|---|---|---|---|
| 315.31 | 76 | −5.3 | 90 | 91 |

N-(furan-2-ylmethyl)-7H-purin-6-amine is highly stable in human plasm and after an exposure to human microsomal fraction. The data from the Caco-2 model of gut wall predict that it will be orally available. Exceptionally high permeability in the MDR1-MDCK model of blood-brain barrier predict excellent CNS permeability probably through a transporter. CNS penetration is key for attaining the effects on the central pacemaker.

Example 11: Dry Capsules Containing
N-(furan-2-ylmethyl)-7H-purin-6-amine and
Melatonin 50 capsules, each containing 500 mg of N-(furan-2-ylmethyl)-7H-purin-6-amine and 5 mg melatonin as active ingrediencies, are prepared as follows:

Composition:
N-(furan-2-ylmethyl)-7H-purin-6-amine 25 g
Melatonin 250 mg
Talc 100 mg
Magnesium stearate 100 mg
Protocol: Homogenized compounds are passed through a sieve with 0.6 mm openings. An amount of 0.51 g of the mixture is put into a gelatin capsule.

The invention claimed is:

1. A method of treatment of jet lag, social jet lag or circadian dysfunction due to shift-work, comprising the step of administering N-(furan-2-ylmethyl)-7H-purin-6-amine, or a pharmaceutically acceptable salt or solvate thereof, to a subject in need of such treatment.

2. The method according to claim 1, wherein N-(furan-2-ylmethyl)-7H-purin-6-amine, or a pharmaceutically acceptable salt or solvate thereof, is administered in a single-dose or in multiple doses over a time period no longer than 5 days.

3. The method according to claim 1, wherein N-(furan-2-ylmethyl)-7H-purin-6-amine, or a pharmaceutically acceptable salt or solvate thereof, is administered together with light therapy.

4. The method according to claim 1, wherein the N-(furan-2-ylmethyl)-7H-purin-6-amine, or a pharmaceutically acceptable salt or solvate thereof, is administered together with a chronotherapeutic selected from melatonin, ramelteon, tasimelteon, agomelatin, harmine and resveratrol.

* * * * *